(12) United States Patent
Wu et al.

(10) Patent No.: US 7,868,145 B2
(45) Date of Patent: Jan. 11, 2011

(54) MAGNETIC PARTICLES CONTAINING A COPOLYMER CORE, MAGNETIC LAYER AND SILICON LAYER

(75) Inventors: Kun Chan Wu, Yuanli Township, Miaoli County (TW); Hui-Ju Cho, Lugang Township, Changhua County (TW); Pei-Shin Jiang, Taichung (TW); Hsiang Yuan Huang, Kaohsiung (TW); Wen-Hsun Kuo, Tainan (TW); Chi-Min Chau, Dadu Township, Taichung County (TW); Chih Hsien Su, Kaohsiung (TW); Kun Feng Lee, Hunei Township, Kaohsiung County (TW)

(73) Assignee: Industrial Technology Research Institute, Hsinchu (TW)

( * ) Notice: Subject to any disclaimer, the term of this patent is extended or adjusted under 35 U.S.C. 154(b) by 692 days.

(21) Appl. No.: 11/822,958

(22) Filed: Jul. 11, 2007

(65) Prior Publication Data

US 2009/0017518 A1   Jan. 15, 2009

(51) Int. Cl.
| | |
|---|---|
| *C07K 1/14* | (2006.01) |
| *C07K 1/22* | (2006.01) |
| *C07K 17/14* | (2006.01) |
| *C07K 17/08* | (2006.01) |
| *C12P 1/00* | (2006.01) |
| *C12N 11/14* | (2006.01) |
| *C12N 11/08* | (2006.01) |
| *G01N 33/553* | (2006.01) |
| *G01N 33/552* | (2006.01) |
| *G01N 33/545* | (2006.01) |

(52) U.S. Cl. ........... 530/412; 530/415; 530/811; 530/815; 435/176; 435/180; 435/814; 436/526; 436/527; 436/531

(58) Field of Classification Search .......... None
See application file for complete search history.

(56) References Cited

U.S. PATENT DOCUMENTS

| | | | | |
|---|---|---|---|---|
| 5,648,124 | A * | 7/1997 | Sutor ............... | 427/475 |
| 6,027,945 | A * | 2/2000 | Smith et al. ....... | 436/526 |
| 6,103,379 | A * | 8/2000 | Margel et al. ..... | 428/403 |
| 6,133,047 | A  | 10/2000 | Elaissari et al. | |
| 6,274,387 | B1 | 8/2001 | Yamauchi et al. | |
| 7,396,589 | B2 * | 7/2008 | Cho et al. ......... | 428/403 |
| 7,410,811 | B2 * | 8/2008 | Lin et al. .......... | 436/526 |
| 7,504,082 | B2 * | 3/2009 | Cho et al. ......... | 423/263 |
| 2007/0087385 | A1 * | 4/2007 | Muller-Schulte ... | 435/7.1 |

OTHER PUBLICATIONS

Iiuang et al. "Preparation and Magnetic Properties of Magnetic Composite Microspheres" Chinese Journal of Inorganic Chemistry vol. 20, No. 3, 2004, pp. 363-P366.

Liu et al. "Preparation and Development of Core-shell Magnetic Nanocomposite Particles" Materials Review, vol. 21, 2007, pp. 183-188.

* cited by examiner

*Primary Examiner*—David M Naff
(74) *Attorney, Agent, or Firm*—Birch, Stewart, Kolasch & Birch, LLP (57) ABSTRACT

A magnetic particle and fabrication method thereof. The magnetic particle comprises a polymer core, a magnetic material layer covering the polymer core, and a silicon containing layer covering the magnetic material layer. In addition, the magnetic particle may further comprise a coupling agent on the silicon containing layer, and an active molecule connected to the coupling agent. The magnetic particles provide controllable size, uniform diameter distribution, high magnetization, improved storage stability, and modified surface for targeting biomolecules for biomaterial separation and environmental analysis.

28 Claims, 9 Drawing Sheets

MAGNETIC PARTICLES CONTAINING A COPOLYMER CORE, MAGNETIC LAYER AND SILICON LAYER

BACKGROUND OF THE INVENTION

1. Field of the Invention

The invention relates to magnetic particles, and in particular to magnetic particles with specific targeting functions for biomaterial separation and fabrication method thereof.

2. Description of the Related Art

Many biological materials such as nucleic acids present special challenges in terms of isolation from natural environments, often being present in very small concentrations and frequently found in the presence of many other solid and dissolved substances.

Accordingly, many procedures and materials for isolation of biological materials have been proposed, such as use of magnetic particles to adsorb biological materials, in which biological materials are agglutinated along with the magnetic particles. The agglutinate is separated from the original solvent by application of a magnetic field and a washing step.

Among several types of magnetic particle for isolating biological materials, an example is U.S. Pat. No. 6,133,047, which discloses superparamagnetic monodispersed particles comprising a core of a first polymer, an internal layer of a second polymer coating the core and in which a magnetic material is distributed, and an external layer of a third polymer coating the magnetic layer and capable of interacting with at least one biological molecule. U.S. Pat. No. 6,274,387 discloses a magnetic carrier comprising particulate silica containing a magnetic material, having polyacrylamide on the surface thereof. The surface of particulate silica containing the magnetic material is treated with a coupling agent, and the treated particulate silica is reacted with acrylamide and/or polyacrylamide. However, the properties of the magnetic particles are not sufficiently controllable.

There remains a need for a magnetic particle with controllable size, uniform diameter distribution, improved storage stability, and modified surface for specific targeting functions.

BRIEF SUMMARY OF THE INVENTION

The invention provides an improved magnetic particle for efficient biomaterial separation, biomaterial purification, drug delivery and environmental analysis. The magnetic particles provide controllable size, uniform diameter distribution, high magnetization, improved storage stability, and modified surface for specific targeting biomolecules.

A magnetic particle comprises a polymer core, a magnetic material layer covering the polymer core, and a silicon containing layer covering the magnetic material layer. The diameter of the magnetic particle is about 0.1 to 5 μm. The magnetic particle may further comprise a coupling agent on the silicon containing layer, and an active molecule connected to the coupling agent.

The invention also provides a method of fabricating the magnetic particle, comprising forming the polymer core by emulsion polymerization of at least one type of monomer, forming the magnetic material layer to cover the polymer core, and forming the silicon containing layer to cover the magnetic material layer. The method may further comprise modifying the surface of the silicon containing layer with a coupling agent, and connecting an active molecule to the coupling agent.

The invention further provides a process for isolating a biomolecule in a biomolecular contained specimen, comprising mixing the magnetic particle of the invention with the biomolecular contained specimen to form a mixture, applying a magnetic field to the mixture, and separating the magnetic particle from the biomolecular contained specimen. The surface of the silicon containing layer is modified with the coupling agent having functional groups to connect the active molecule, thus enhancing efficiency of biomaterial separation.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a magnetic particle suitable for biomaterial separation and environmental analysis. The surfaces of the magnetic particles are modified to connect with specific materials or biomolecules. For example, the magnetic particles can be applied to separate biomaterial from blood, wherein the modified surfaces can bind specific biomolecules in the blood, and enhance the separation efficiency by magnetism. The magnetic particles can be applied to environmental analysis, for example, isolate contaminants in water.

Figure 1:
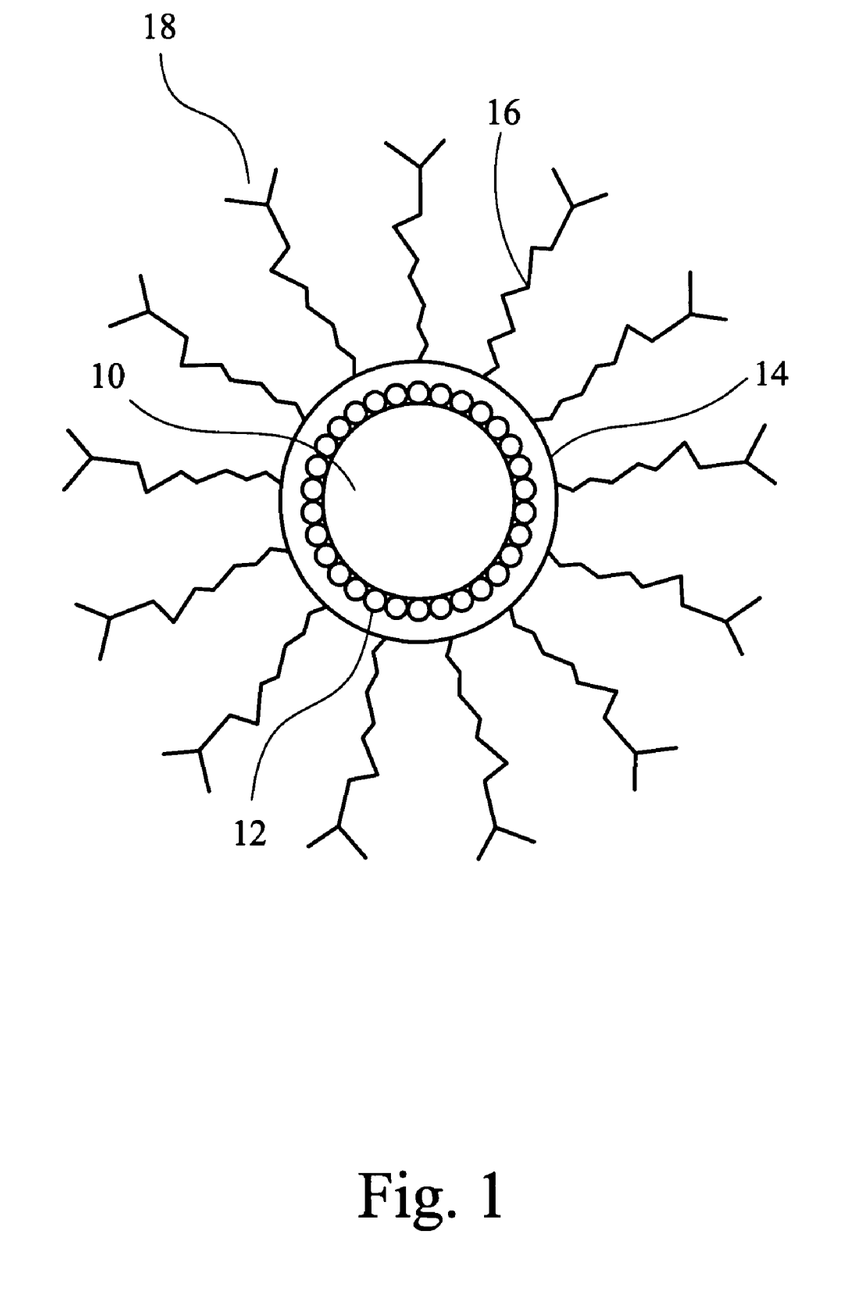
FIG. 1 is a schematic cross section of a magnetic particle according to an embodiment of the invention.

Referring to FIG. 1, a magnetic particle comprises a polymer core 10, a magnetic material layer 12 covering the polymer core, and a silicon containing layer 14 covering the magnetic material layer. The diameter of the magnetic particle is about 0.1 to 5 μm. The polymer core may be a homopolymer or a copolymer, derived from monomers such as styrene, styrene derivatives, alkylacrylate, alkylmethacrylate, N-alkylacrylamide, or N,N-dialkyl-acrylamide, wherein the alkyl group can be $C_{3-20}$ alkyl. The monomers of styrene and styrene derivatives are particularly preferred. The styrene derivatives include methyl styrene, ethyl styrene, tert-butyl styrene, chloromethylstyrene or di-vinyl benzene. The magnetic material layer may be paramagnetic, superparamagnetic, ferromagnetic or ferritemagnetic material. Suitable magnetic materials include metal oxides of iron, titanium, cobalt, zinc, copper, manganese, or nickel, magnetite; hematite, ferrites such as manganese, nickel or manganese-zinc ferrites, or alloys of cobalt or nickel. The silicon containing layer covering the magnetic material layer can fix the magnetic particles on core surface, enhance the storage stability of the magnetic particles, and ease modification of surfaces of the magnetic particles. The silicon containing layer may be siloxane, silica glass, silicon oxide, silicate salts or the like.

As shown in FIG. 1, the magnetic particle may further comprise a coupling agent 16 on the silicon containing layer, and an active molecule 18 connected to a functional group of the coupling agent. The coupling agent can be functional silane. The functional group of the coupling agent 16 includes amine, thiol, hydroxyl, aldehyde, carboxylic, ester or the like, which can connect to the active molecule 18. The active molecule 18 has affinity to adsorb specific materials, biomolecules or cells. The active molecule includes, but is not limited to, antibody, nucleic acid, oligonucleotide, protein, sugar or antigen.

In an exemplary method of fabricating the magnetic particles according to the invention, the polymer core can be synthesized by emulsion polymerization of at least one type of monomer as described. For example, styrene can be reacted with methylacrylic acid (MAA) in a mixture of water and ethanol to synthesize a plurality of polystyrene cores having carboxylic acid groups thereon by emulsion polymerization. The ratio of water to ethanol and the amount of styrene can be adjusted to obtain various diameters of the polymer cores, such that diameter of the polymer core can be about 200 to 5000 nm and the diameter distribution is uniform. Second, magnetic material precursors are adsorbed uniformly on the surfaces of the polymer core via functional groups on the polymer core. The functional groups on the polymer core may be amine, hydroxyl, carboxylic or the like. Then, the magnetic material precursors are converted to a magnetic material layer by chemical reaction to cover the polymer core. For example, $Fe^{2+}$ ions are adsorbed uniformly on the surface of each polystyrene core via the carboxylic acid groups of the core. Then $Fe^{2+}$ ions are formed into $Fe_3O_4$ as the magnetic material layer covering the core. The thickness of the magnetic material layer is about 15 to 30 nm. Subsequently, a silicon containing layer is formed to cover the magnetic material layer. The thickness of the silicon containing layer is about 20 to 30 nm. The silicon containing layer may be siloxane, silica glass, silicon oxide or silicate salts which can be formed from a silicon containing precursor. The silicon containing precursor includes silicon alkoxide, sodium silicate, 3-aminopropinyl silane, vinyltrichlorosilane, trimethoxyvinylsilane, triethoxyvinylsilane, tris(2-methoxyethoxy)vinylsilane, 3-glycidoxypropyltrimethoxysilane, 3-methacryloxypropyltrimethoxysilane, diethoxy-3-glycidoxypropylmethylsilane or combinations thereof, wherein silicon alkoxide is such as $Si(OCH_3)_4$, $Si(OC_2H_5)_4$, $Si(O-n-C_3H_7)_4$, $Si(O-i-C_3H_7)_4$, $Si(O-n-C_4H_9)_4$, or $Si(O-i-C_4H_9)_4$. For example, $Si(OC_2H_5)_4$ (Tetraethyl orthosilicate (TEOS)) is added as precursor of the silicon containing layer to cover the magnetic material layer into the magnetic particle.

The surface of the silicon containing layer may be modified with a coupling agent. The coupling agent has a functional group including amine, thiol, hydroxyl, aldehyde, carboxylic, ester or the like. An active molecule can be connected to the coupling agent on the magnetic particle such that specific biomolecules can be bound in a biomolecular contained specimen. The bound biomolecules may be antibody, nucleic acid, oligonucleotide, protein, sugar or antigen. For example, the silicon containing layer of the magnetic particles can be modified with coupling agent of (3-aminopropyl)triethoxysilane (APTES). Then the end group of APTES is converted to carboxylic acid group and connected to the active molecule of antibody to bind antigens in blood.

The magnetic particles according to the invention can isolate a biomolecule in the biomolecular contained specimen. First, the magnetic particles including the active molecule thereon are mixed into a biomolecular contained specimen to form a mixture, wherein the biomolecule in the biomolecular contained specimen is bound to the active molecule. Then a magnetic field is applied to the mixture, and the magnetic particles binding the biomolecule are separated from the biomolecular contained specimen.

Without intending to limit it in any manner, the invention is further illustrated by the following examples.

EXAMPLE 1

Figure 3:
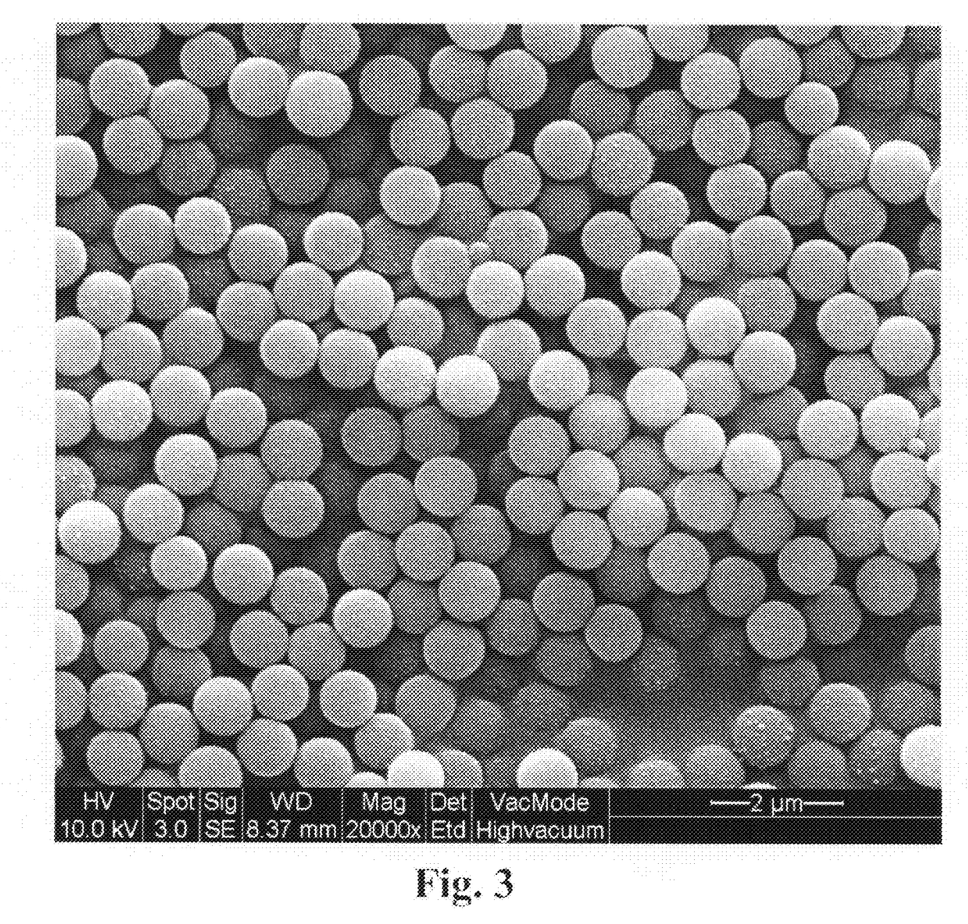
FIG. 3 is a SEM photograph of the polymer cores of Example 1 with diameter of 921.6±75.3 nm.

Polymer Core Preparation 18 ml of styrene, 1 ml of methylacrylic acid, 0.1 g of $K_2S_2O_8$, 10 ml of ethanol, and 60 ml of deionized water were placed in a reaction vase. Under nitrogen, the mixture was stirred at 70° C. for reaction for 24 hours, and then cooled to room temperature to obtain polystyrene cores. The polymer cores were observed by SEM to measure the diameter thereof. The SEM photograph of the polymer cores according to the above reaction condition is shown in FIG. 3. As shown, the diameter of the polymer core is about 921.6±75.3 nm, and diameter distribution is uniform.

Figure 2:
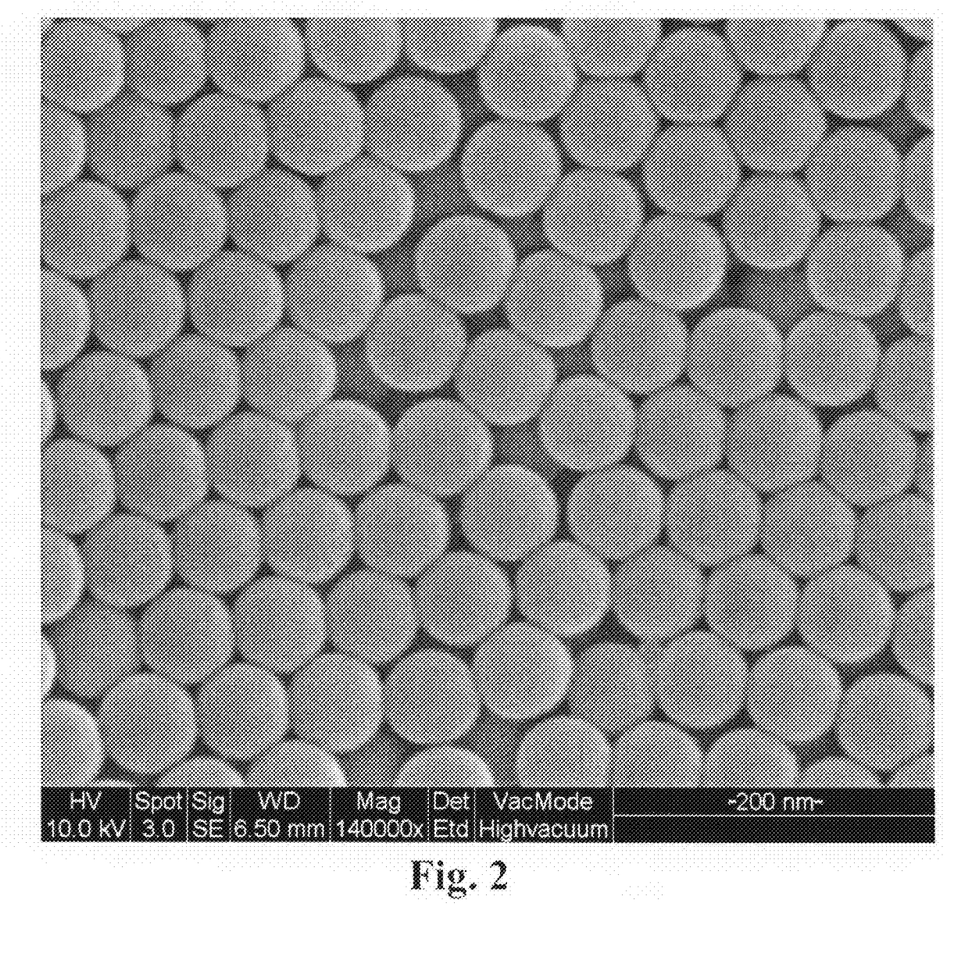
FIG. 2 is a SEM photograph of the polymer cores of Example 1 with diameter of 220.4±6.5 nm.

The reaction condition can be adjusted such that a ratio of water to ethanol is 7:0 and the mixture was stirred at 80° C. for reaction for 24 hours with other conditions remaining, resulting in the diameter of the obtained polymer core was about 220.4±6.5 nm. SEM photograph of the polymer cores according to the second reaction condition is shown in FIG. 2. The diameter distribution of the second polymer cores is also uniform.

EXAMPLE 2

Figure 4:
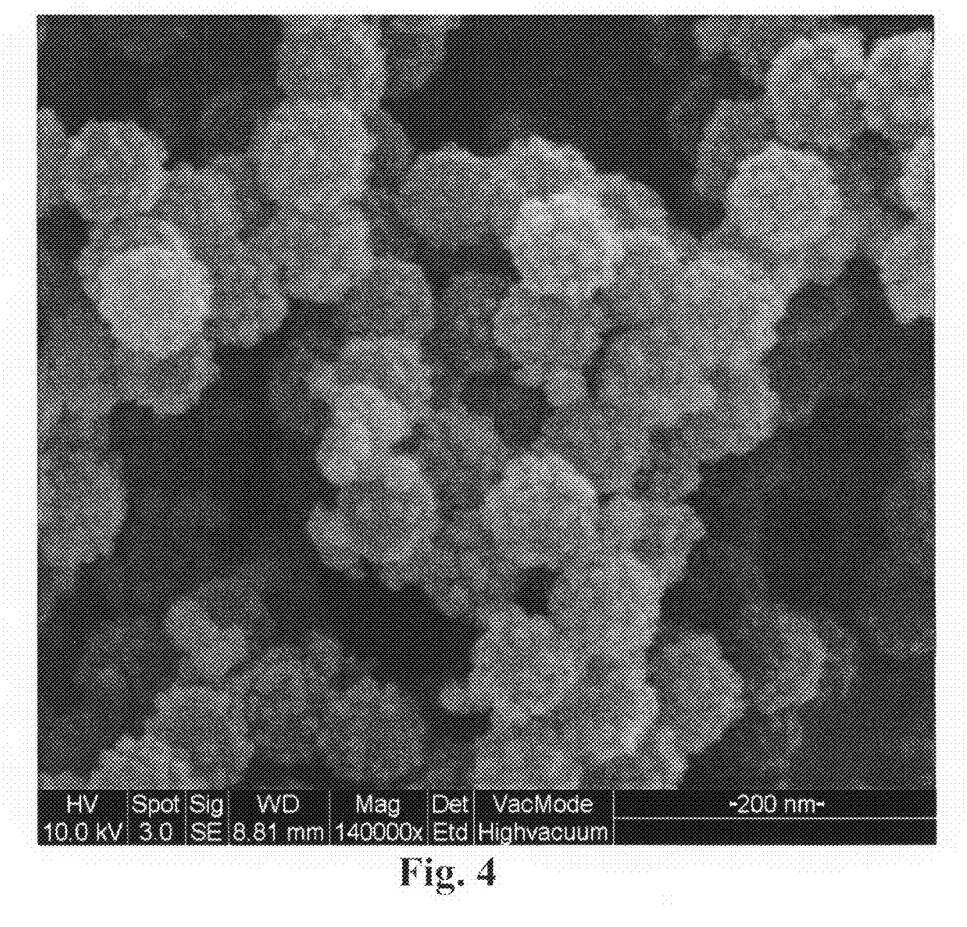
FIG. 4 is a SEM photograph of covering the polymer cores of FIG. 2 with magnetic material layer of Example 2, which have overall diameter of 250.4±7.2 nm.
Figure 5:
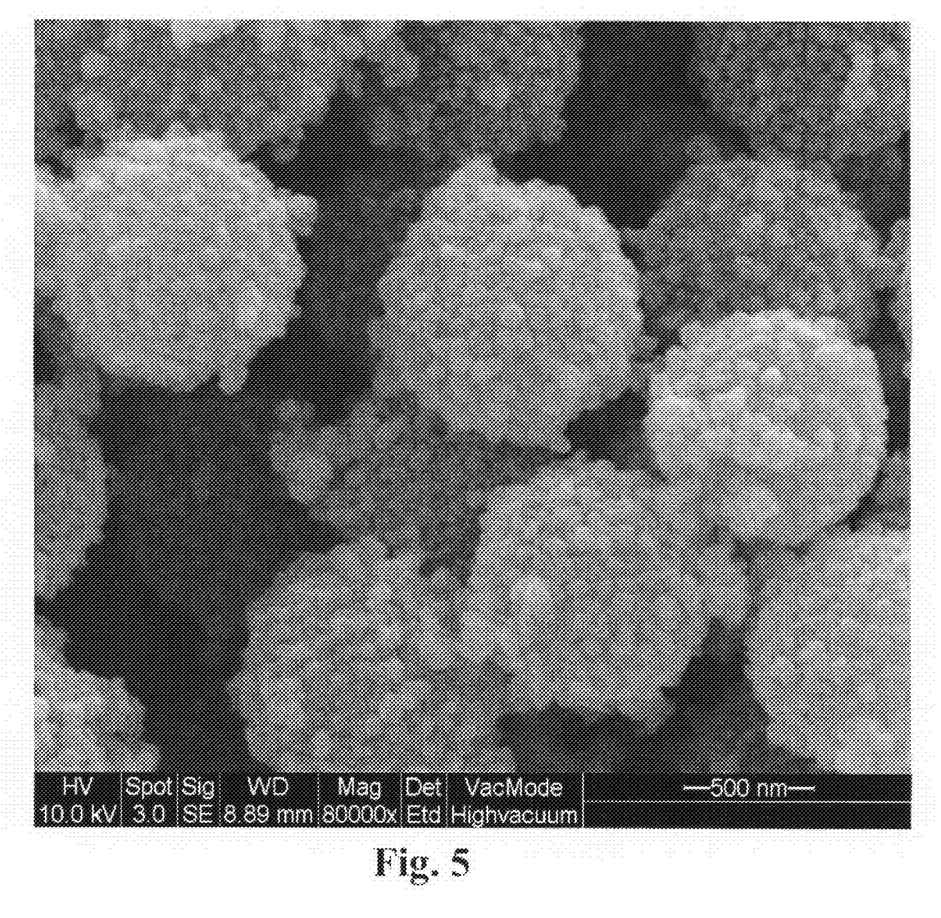
FIG. 5 is a SEM photograph of covering the polymer cores of FIG. 3 with magnetic material layer of Example 2, which have overall diameter of 950.0±77.2 nm.

Covering the Polymer Core With Magnetic Material Layer 200 mg of polystyrene core of Example 1 and 30 ml ethylene glycol were agitated for 10 minutes by ultrasonic wave and 120 ml of deionized water was added. Subsequently, 2 g of hexamethylenetetramine, 0.1 g of $KNO_3$, and 1 g of $FeCl_2$ were added to the mixture at 80° C. for reaction for 4 hours. After the reaction completed, the product was washed by deionized water to obtain a magnetic material layer of $Fe_3O_4$ covering the polystyrene core. FIG. 4 is a SEM photograph of covering the polymer cores of diameter of 220.4±6.5 nm with magnetic material layer. The overall diameter of the particles in FIG. 4 was about 250.4±7.2 nm and saturation magnetization was 61.3 emu/g. FIG. 5 is SEM photograph of covering the polymer cores of diameter of 921.6±75.3 nm with magnetic material layer, with overall diameter of about 950±77.2 nm and saturation magnetization of 52.3 emu/g. The thickness of the magnetic material layer was about 30 nm.

EXAMPLE 3

Figure 6:
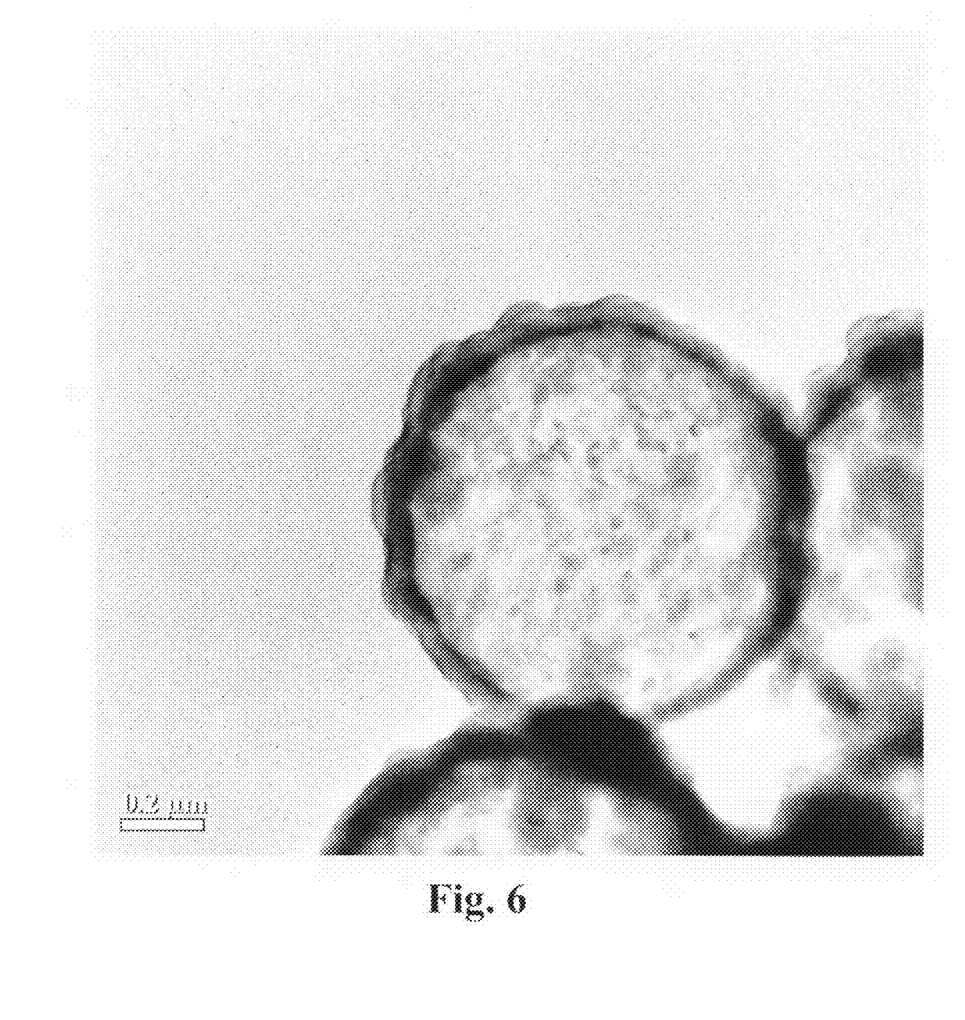
FIGS. 6 and 7 are TEM photographs of the magnetic particles, covering the magnetic material layer with the silicon containing layer of Example 3.
Figure 7:
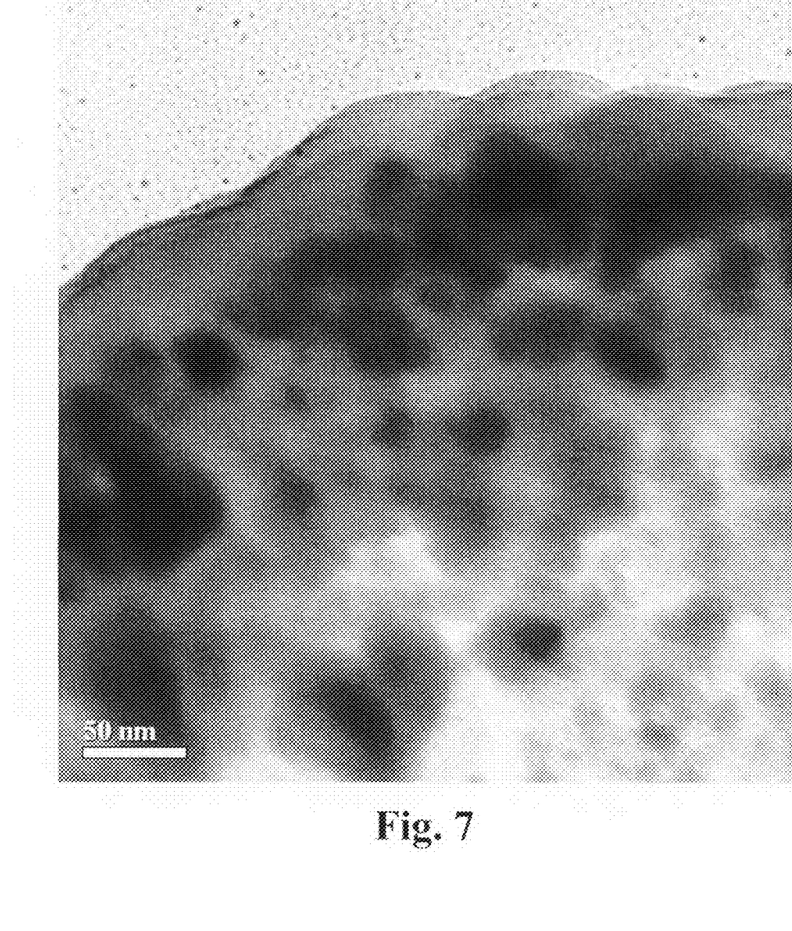
Figure 8:
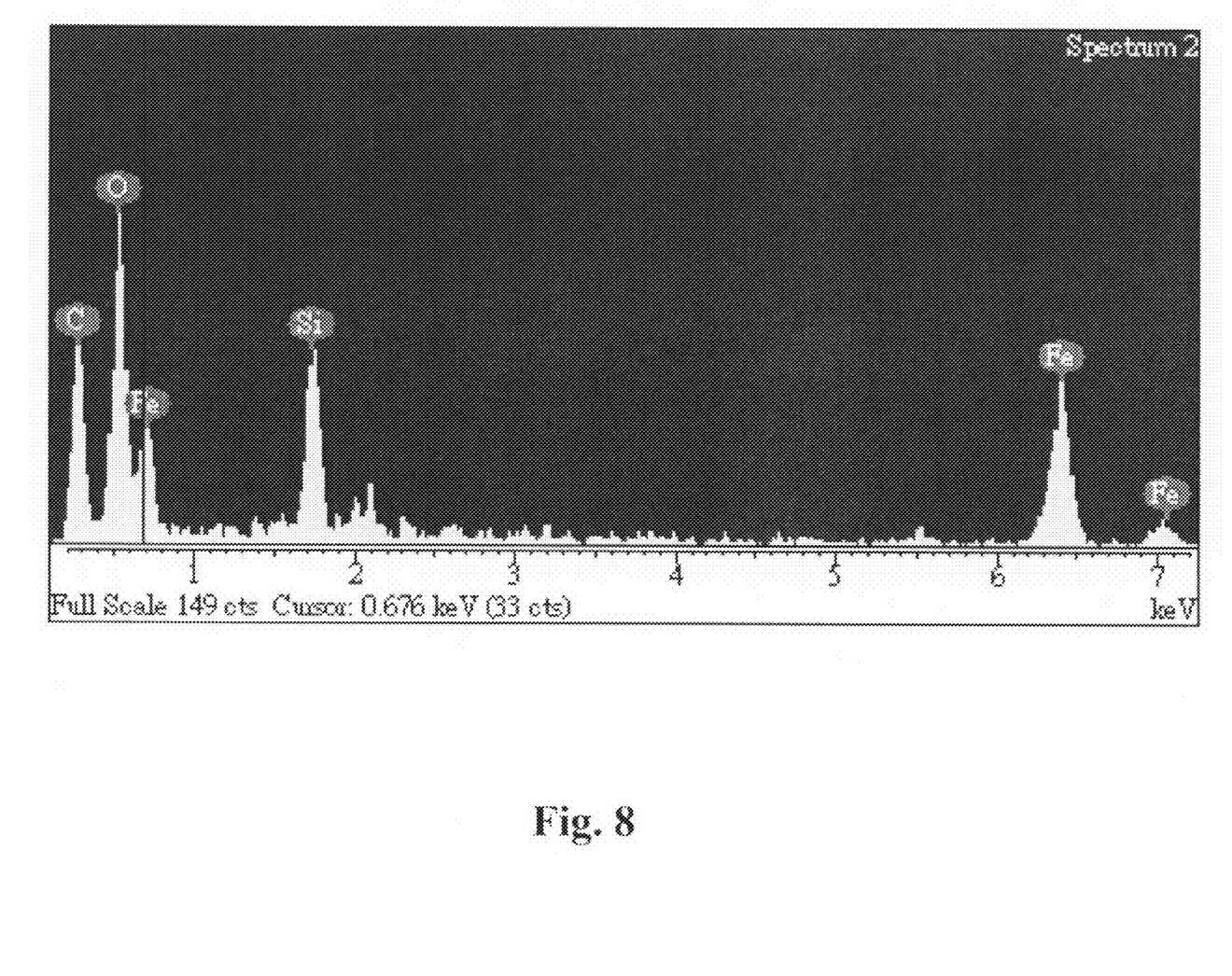
FIG. 8 is a EDX ultimate analysis spectrogram of the magnetic particles of Example 3.

Covering the Magnetic Material Layer With Silicon Containing Layer 50 mg of Example 2, 50 ml of deionized water, and 1.25 g of polyvinylpyrrolidone (PVP-10) were placed in a reaction vase, and stirred at 600 rpm for 24 hours for reaction. The solid product was separated by centrifuge, and 50 ml of ethanol was added to the solid product into a mixture. Subsequently, 2.42 ml solution of 4.2% ammonia water in ethanol, and a solution of 10% tetraethyl orthosilicate (TEOS) in ethanol were added and stirred for reaction for 15 hours to obtain a silicon containing layer covering the magnetic material layer into the magnetic particles of invention. FIGS. 6 and 7 are TEM photographs of covering the magnetic material layer with the silicon containing layer. FIG. 8 is EDX ultimate analysis spectrogram of Example 3. As shown in FIG. 8, there were at least three peaks of Si, O and Fe of the magnetic particles, indicating formation of the silicon containing layer thereon.

EXAMPLE 4

Coupling With Coupling Agent

The magnetic particles of Example 3 and a solution of 20% (3-aminopropyl)triethoxysilane (APTES) in ethanol were stirred for reaction for 15 hours. After the reaction completed, the product was washed by ethanol and deionized water 3 times respectively to obtain the magnetic particles with coupling agent of APTES thereon. Then, functional groups of APTES were converted to carboxylic acid groups.

EXAMPLE 5

Coupling With Active Molecule 1 g of the magnetic particles with carboxylic acid group thereon of Example 4 was washed by 25 mM, pH 5 MES buffer solution, stirred, for 5 minutes, and then removed from solution by a magnetic separator. The step was repeated twice. Subsequently, the washed magnetic particles, 50 μl of 50 mg/ml N-Ethyl-N'-(3-dimethylaminopropyl)carbodiimide (EDC), and 50 μl of 50 mg/ml Hydroxy-2,5-dioxopyrrolidine-3-sulfonic acid sodium salt (sulfo-NHS) were stirred 30 minutes for reaction, then washed by 25 mM, pH 5 MES buffer solution 2 times.

100 μl of 900 μg/ml C-reactive protein (CRP) antibody solution and the magnetic particles treated as described were stirred 2 hours for reaction, and the non-reactive antibody solution was removed. Subsequently, 100 μl of 1M, pH 7.4 Tris solution was added for reaction 0.5 hours, and then washed by 0.01M, pH 7.4 PBS buffer solution into 10 mg/ml solution of magnetic particles with surfaces modified with CRP antibody. The surfaces of 1 mg of magnetic particles can be fixed about 30 μg of active CRP antibody.

EXAMPLE 6

Biomolecule Bound Test

Figure 9:
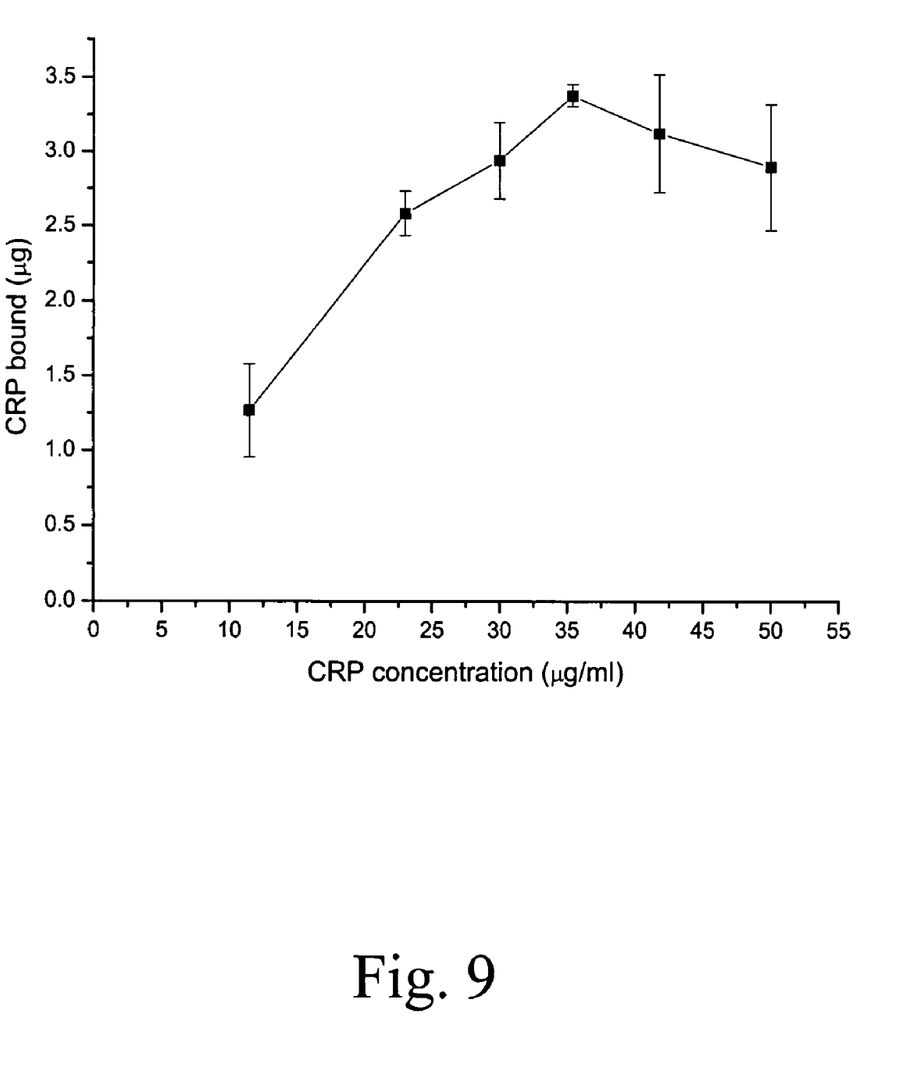
FIG. 9 is a plot of the amount of bound CRP using the magnetic particles of the invention versus CRP concentration of original solution.

100 μl of solution of magnetic particles which surfaces were modified with CRP antibody of Example 5 was placed in a magnetic separator to remove the buffer solution thereof. Several concentration of CRP solution were adjusted by 0.01M, pH 7.4 PBS buffer solution, and mixed to the magnetic particles treated as above. The specific active molecule of the CRP antibody on the magnetic particles can bind CRP in the solution. After 1 hour of reaction, the mixture was placed in a magnetic separator, and the non-reactive CRP solution collected to measure the amount of CRP, after which the amount of CRP bound by the magnetic particles can be estimated. FIG. 9 is a plot of the amount of CRP bound versus CRP concentration of original solution. As the result of the CRP bound test, the bound efficiency of the magnetic particles modified with CRP antibody thereon is higher than 95.4%.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A magnetic particle, comprising:
   a copolymer core polymerized of styrene and methylacrylic acid;
   a magnetic material layer covering the copolymer core; and
   a silicon containing layer covering the magnetic material layer.

2. The magnetic particle as claimed in claim 1, having a diameter from 0.1 to 5 μm.

3. The magnetic particle as claimed in claim 1, wherein the copolymer core has a diameter from 200 to 5000 nm.

4. The magnetic particle as claimed in claim 1, wherein the magnetic material layer has a thickness of at least 15 nm.

5. The magnetic particle as claimed in claim 1, wherein the silicon containing layer has a thickness of at least 20 nm.

6. The magnetic particle as claimed in claim 1, wherein the magnetic material layer comprises paramagnetic, superparamagnetic, ferromagnetic, or ferritemagnetic material.

7. The magnetic particle as claimed in claim 1, wherein the silicon containing layer comprises siloxane, silica glass, silicon oxide or silicate salts.

8. The magnetic particle as claimed in claim 1, further comprising a coupling agent on the silicon containing layer.

9. The magnetic particle as claimed in claim 8, further comprising an active molecule connected to the coupling agent.

10. The magnetic particle as claimed in claim 8, wherein the coupling agent comprises functional silane.

11. The magnetic particle as claimed in claim 8, wherein the coupling agent contains a functional group comprising amine, thiol, hydroxyl, aldehyde, carboxylic, or ester.

12. The magnetic particle as claimed in claim 9, wherein the active molecule comprises antibody, nucleic acid, oligonucleotide, protein, sugar or antigen.

13. A method of fabricating the magnetic particle as set forth in claim 1, comprising:
    forming the copolymer core by emulsion polymerization of styrene and methylacrylic acid;
    forming the magnetic material layer to cover the copolymer core; and
    forming the silicon containing layer to cover the magnetic material layer.

14. The method as claimed in claim 13, wherein the magnetic particle has a diameter from 0.1 to 5 μm.

15. The method as claimed in claim 13, wherein a diameter of the copolymer core is controlled to be 200 to 5000 nm by a solvent ratio of water to ethanol.

16. The method as claimed in claim 13, wherein the magnetic material layer has a thickness of at least 15 nm.

17. The method as claimed in claim 13, wherein the silicon containing layer has a thickness of at least 20 nm.

18. The method as claimed in claim 13, wherein the magnetic material layer comprises paramagnetic, superparamagnetic, ferromagnetic or ferritemagnetic material.

19. The method as claimed in claim 13, wherein the silicon containing layer comprises siloxane, silica glass, silicon oxide or silicate salts.

20. The method as claimed in claim 19, wherein the silicon containing layer is formed from a silicon containing precursor.

21. The method as claimed in claim 20, wherein the silicon containing precursor comprises silicon alkoxide, sodium silicate, 3-aminopropinyl silane, vinyltrichlorosilane, trimethoxyvinylsilane, triethoxyvinylsilane, tris(2-methoxyethoxy)vinylsilane, 3-glycidoxypropyltrimethoxysilane, 3-methacryloxypropyltrimethoxysilane, diethoxy-3-glycidoxypropylmethyllsilane or combinations thereof.

22. The method as claimed in claim 21, wherein the silicon alkoxide comprises $Si(OCH_3)_4$, $Si(OC_2H_5)_4$, $Si(O\text{-}n\text{-}C_3H_7)_4$, $Si(O\text{-}i\text{-}C_3H_7)_4$, $Si(O\text{-}n\text{-}C_4H_9)_4$, or $Si(O\text{-}i\text{-}C_4H_9)_4$.

23. The method as claimed in claim 13, further comprising modifying the surface of the silicon containing layer with a coupling agent, and connecting an active molecule to the coupling agent.

24. The method as claimed in claim 23, wherein the coupling agent comprises functional silane.

25. The method as claimed in claim 23, wherein the coupling agent contains a functional group comprising amine, thiol, hydroxyl, aldehyde, carboxylic, or ester.

26. The method as claimed in claim 23, wherein the active molecule comprises antibody, nucleic acid, oligonucleotide, protein, sugar or antigen.

27. A process for isolating a biomolecule in a biomolecular contained specimen, comprising:
    mixing the magnetic particle as set forth in claim 8 with the biomolecular contained specimen to form a mixture;
    applying a magnetic field to the mixture; and
    separating the magnetic particle from the biomolecular contained specimen.

28. The process as claimed in claim 27, wherein the biomolecule of the biomolecular contained specimen comprises protein, antibody, nucleic acid, oligonucleotide, sugar or antigen.

* * * * *